June 16, 1953 C. D. CORLISS Plant Pat. 1,195
EUONYMUS FORTUNEI PLANT
Filed Jan. 4, 1951
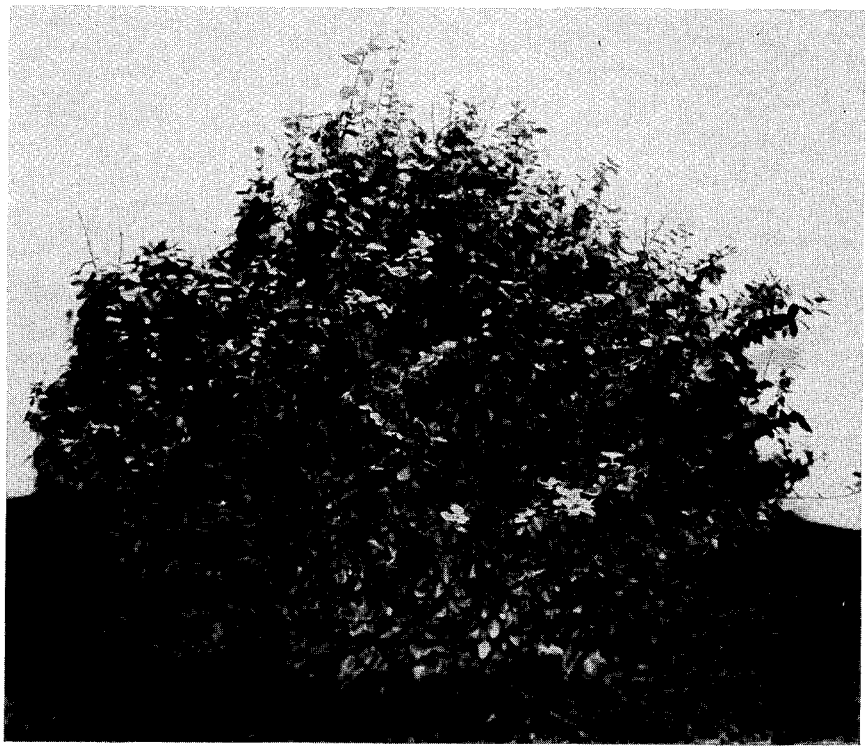
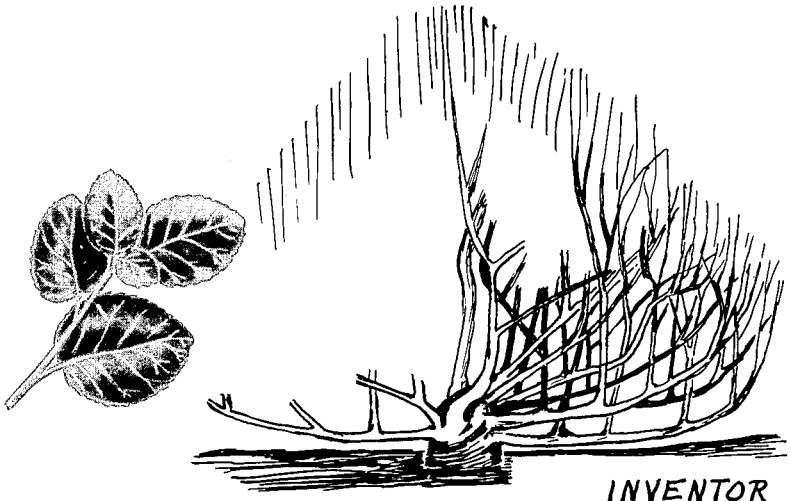
INVENTOR
Clifford D. Corliss
By Orville M. Kile
Plant Pat. Agt.

Patented June 16, 1953

Plant Pat. 1,195

UNITED STATES PATENT OFFICE 1,195

EUONYMUS FORTUNEI PLANT

Clifford D. Corliss, Gloucester, Mass., assignor to Corliss Bros., Inc., Gloucester, Mass., a corporation of Massachusetts Application January 4, 1951, Serial No. 204,410

1 Claim. (Cl. 47—59)

My present invention relates to a new and distinct variety of evergreen Euonymus plant of the shrub type, originated by me as a selected seedling. It is a cross between *Euonymus fortunei radicans* and *fortunei vegeta*, having been produced and asexually reproduced from cuttings at nurseries in Gloucester, Massachusetts.

Although both parents are of the essentially prostrate and viney type of growth, my new variety grows in a naturally erect position without the necessity of support or clipping. The parent *radicans* is notably prostrate and vining and while the other parent *vegeta* for the first few years of its growth may stand rather erect but with prostrate branches from the base, it soon begins to vine and unless supported or clipped the branches fall to the ground and produce an essentially prostrate form. Virtually all of the growth of my new variety comes from one main stem branching uniformly in all directions. Its symmetrical, rounded form—broader than tall—makes it particularly adapted for foundation plantings of homes and buildings and in landscape plantings, especially where a semi-dwarf shrub is desired. Probably its most outstanding distinguishing feature is its extreme compactness or density of growth all the way to the ground.

My new variety is exceptionally hardy, easily transplanted, and tolerant of either dry or moist locations and of sun and partial or semi-shade, and is adaptable to almost any type of soil.

This new variety is easily propagated. The only means of reproduction is asexual and young plants thus produced at our Gloucester location exhibit the same characteristics as the original plant and appear to be permanently fixed through succeeding generations.

The accompanying illustration depicts the original plane of my new variety of Euonymus and shows specifically its low, compact, bushy, and symmetrical growth which extends upright without support. Shown in the lower left-hand corner is a twig of the new plant in approximately true colors. In the lower center is a diagrammatical sketch showing the growth of the plant from a central stem.

Following is a detailed description of my new variety. Color plate designations indicate Ridgway's Color Standards and Nomenclature.

Growth:

*Form.*—Naturally erect, somewhat globular, with generally low, wide outline and growing very close to ground. Symmetrical and compact shrub, broader than tall. Grows from one main stem, branching uniformly in all directions.

*Habit.*—Slow-growing and free-branching to form an exceedingly compact bush. Retains its upright form without shearing or clipping and without support. Although this variety will root where its branches come in contact with the ground, just as the prostrate forms of Euonymus do, new growth from these roots will grow upright naturally.

*Size.*—Semi-dwarf. The original plant of this variety has in 14 years reached 3½ feet in height and 4 feet in spread at its base.

Tolerance and resistance: This variety is extremely hardy, having withstood extremely low temperatures in Massachusetts with no sign of winter burn or other ill effects. Growth under extremely dry conditions has shown its drought resistance and it has likewise proved tolerant of moist conditions. It has grown well either in the sun or in a great degree of shade, and appears to thrive equally well in sand, clay or loam soil.

Roots: Strong, fibrous root system enables this variety to be easily and successfully transplanted, either with bare roots or with a good ball of earth.

Branches: More numerous than on any other similar variety; growing very closely spaced in all directions from a central stem, which with its many branchlets and leaves produces an extremely dense bush.

Branchlets: Medium green; minutely verruculose.

*Buds.*—Ovate; pointed; length 5 mm.

*Bud scales.*—Pale green and imbricated.

Leaves:

*Type.*—Broadleaf evergreen.

*Size.*—2.5 cm. long.

*Quantity.*—Abundant—this feature adding much to the great density of the plant.

*Position.*—Opposite. Mostly imbricated and lying flat against each other. The position of the leaves gives the bush the appearance of being "matted."

*Shape.*—Have general appearance of leaves of *Euonymus fortunei radicans* but are somewhat wider, indicating the *Euonymus fortunei vegeta* parentage. Broadly ovate, with acute apex and usually a rounded base. Margin crenate, very slightly revolute.

*Texture.*—Leathery.

*Color.*—Glossy, dark green above, approximately Grass Green (Pl. VI), with veins distinct and considerably lighter. Under surface light green, approximately Biscay Green (Pl. XVII), and with dull aspect.

*Petioles.*—From 3 to 5 mm. long.

Internodes: Length 1.5 cm. to 2.5 cm.

Fruit: Entirely lacking.

Having thus disclosed my invention, I claim:

The new and distinct variety of Euonymus plant, substantially as herein shown and described, characterized particularly by its natural and distinctly erect growth without the necessity of support or clipping; its habit of symmetrical and uniform branching in all directions from a central trunk, forming a generally low, compact, semi-dwarf bush which is broader than tall; its great density of branches and leaves which lie flat and imbricated; its small, wide leaves of glossy, dark green color with much lighter veins; its exceptional hardiness, absence of winter burn, and drought resistance; its ease of propagation and transplantation; its excellent adaptability to different conditions of soil, temperature, sun and moisture, and the complete absence of fruits.

CLIFFORD D. CORLISS.

No references cited.